US00PP31413P2

(12) United States Plant Patent
Bak et al.

(10) Patent No.: US PP31,413 P2
(45) Date of Patent: Jan. 28, 2020

(54) ***MEDINILLA* PLANT NAMED 'ROYAL TWIST'**

(50) Latin Name: *Medinilla magnifica*
Varietal Denomination: ROYAL TWIST

(71) Applicants: Elly Bak, Rijsenhout (NL); Nicolaas D. M. Steur, Oude Niedorp (NL)

(72) Inventors: Elly Bak, Rijsenhout (NL); Nicolaas D. M. Steur, Oude Niedorp (NL)

(73) Assignee: CornBak BV (NL)

( * ) Notice: Subject to any disclaimer, the term of this patent is extended or adjusted under 35 U.S.C. 154(b) by 0 days.

(21) Appl. No.: 15/999,224

(22) Filed: Aug. 16, 2018

(51) Int. Cl.
*A01H 5/02* (2018.01)
*A01H 6/00* (2018.01)

(52) U.S. Cl.
USPC ..... Plt./263.1

(58) Field of Classification Search
USPC ..... Plt./263.1, 226
CPC ..... A01H 5/02; A01H 5/00; A01H 6/00
See application file for complete search history.

(56) References Cited

PUBLICATIONS

Upov Pluto Plant Variety Database 20190604, retrieved on Jun. 4, 2019, retrieved from the Internet at www3.wipo.int/pluto/user/en/index.jsp, one page. (Year: 2019).*

* cited by examiner

*Primary Examiner* — June Hwu
(74) *Attorney, Agent, or Firm* — Cassandra Bright

(57) ABSTRACT

A new and distinct *Medinilla* cultivar named 'ROYAL TWIST' is disclosed, characterized by an erect and sturdy plant habit. Glossy, green foliage is approximately 16 cm in length. Pendulous panicles are composed of flowers colored near Red-Purple 64C. The new variety is a *Medinilla*, normally produced as an ornamental plant.

2 Drawing Sheets

Latin name of the genus and species: *Medinilla magnifica*.
Variety denomination: 'ROYAL TWIST'.

BACKGROUND OF THE INVENTION

The present invention relates to a new and distinct hybrid cultivar of *Medinilla* plant, botanically known as *Medinilla magnifica*, hereinafter referred to by the cultivar name 'ROYAL TWIST'. The genus of *Medinilla* belongs to the Melastomataceae family.

The new *Medinilla* 'ROYAL TWIST' is a product of a planned breeding program conducted by the inventors, Elly Black and Nico D. M. Steur, in Assendelft, The Netherlands. The seed parent is the *Medinilla* selection designated '82347005' (unpatented). The pollen parent is the *Medinilla* selection designated '82341131' (unpatented). The objective of the breeding program was to produce a new *Medinilla* variety with a good growing habit and an attractive inflorescence. The crossing was made in 2008.

'ROYAL TWIST' was discovered and selected by the inventors in 2010, as a single flowering plant, at a research greenhouse in Assendelft, The Netherlands.

Asexual reproduction of the new *Medinilla magnifica* 'ROYAL TWIST' by vegetative means by terminal shoots was first performed in 2013 Assenfeldt, the Netherlands. Subsequent propagation has demonstrated that the combination of characteristics as herein disclosed for the new cultivar are firmly fixed and retained through successive generations of asexual reproduction. The new cultivar reproduces true-to-type.

BRIEF DESCRIPTION OF THE INVENTION

The following traits have been repeatedly observed and are determined to be the unique characteristics of 'ROYAL TWIST' which in combination distinguish this *Medinilla magnifica* as a new and distinct cultivar:

1. Solid growth habit; plants are sturdy and not leggy.
2. Erect plant, measuring about 35 cm in height (above the pot when first flowering);
3. Glossy green colored leaves, measuring about 16 cm in length.
4. Pendulous panicles with red-purple (RHS 64C) colored flowers.

COMPARISON TO PARENT PLANTS

The female and male parents are no longer available for comparison.

COMMERCIAL COMPARISON

Of the commercial cultivars known to the present inventors, the most similar in comparison to the new *Medinilla* 'ROYAL TWIST' is the *Medinilla* 'DOLCE VITA' , unpatented. Plants of the new *Medinilla* 'ROYAL TWIST' differ from plants of *Medinilla* 'DOLCE VITA' in the following ways:

1. Plants of 'ROYAL TWIST' are larger than 'DOLCE VITA'.
2. Plants of 'ROYAL TWIST' are taller than 'DOLCE VITA'.

BRIEF DESCRIPTION OF THE PHOTOGRAPHS

The accompanying photographs illustrate the overall appearance of the new *Medinilla* 'ROYAL TWIST' showing the colors as true as is reasonably possible with colored reproductions of this type. Colors in the photographs may differ slightly from the color values cited in the detailed botanical description which accurately describes the color of 'ROYAL TWIST'.

Figure 1:
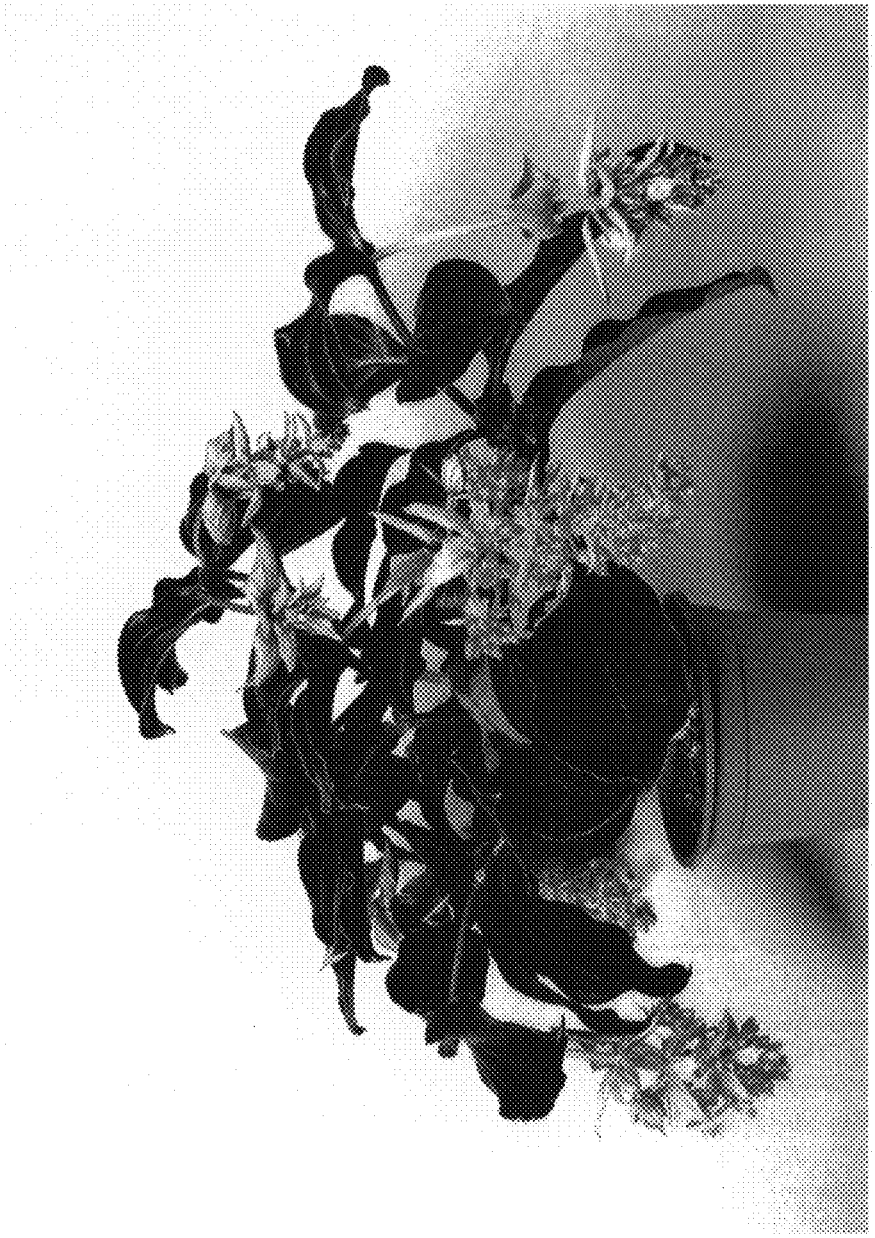

FIG. 1. shows a side view perspective of a typical potted flowering plant of 'ROYAL TWIST' at about 50 weeks from potting.

Figure 2:
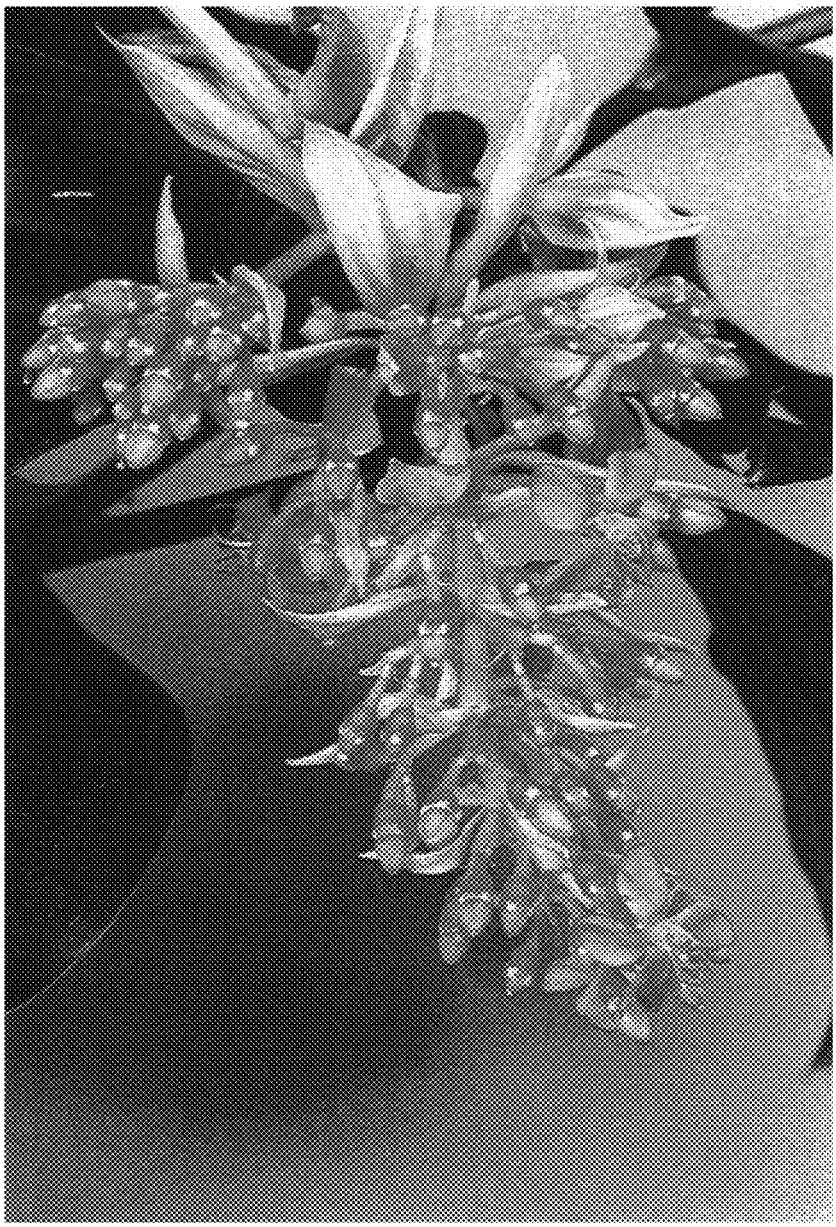

FIG. 2. shows a side view perspective of a typical inflorescence of 'ROYAL TWIST' at about 50 weeks from potting.

DETAILED BOTANICAL DESCRIPTION

'ROYAL TWIST' has not been observed under all possible environmental conditions. The phenotype of the new cultivar may vary with variations in environment such as temperature, light intensity, day length, fertilizers and humidity without any change in the genotype of the plant.

The aforementioned photograph, together with the following observations, measurements and values describe the new *Medinilla* 'ROYAL TWIST' as grown in a greenhouse in Assendelft, the Netherlands, under conditions which closely approximate those generally used in a commercial practice.

Color references are made to The Royal Horticultural Society Colour Chart (R.H.S.), 2001 Edition, except where general colors of ordinary significance are used. Color values were taken under daylight conditions in a greenhouse in Assendelft, The Netherlands. The age of the plants of 'ROYAL TWIST' described is about 50 weeks from potting.

Botanical classification: *Medinilla magnifica* 'ROYAL TWIST'.

Parentage:

*Female parent.*—*Medinilla* selection designated '82347005' (unpatented).

*Male parent.*—*Medinilla* selection designated '82341131' (unpatented).

Propagation: Cuttings.

Plant:

*General appearance and form.*—Height: About 35 cm. Diameter: About 60 cm. Shape: Outwardly erect, overall elliptic. Growth Habit: Tender indoor flowering ornamental. Plant Vigor: Good. Flowering Season: From April until October. Cold Tolerance: Frost tender, temperatures below 5° C. may damage plants. Fragrance: None.

Quantity of primary lateral branches: Average: 2.

Characteristics of primary lateral branches:

*Diameter.*—About 15 mm.

*Shape.*—Quandrangular, winged.

*Width of wings.*—About 3 mm.

*Color.*—Green; near RHS 137B with lignified parts near Grey-Brown 199B.

Foliage:

*Arrangement.*—Opposite.

*Overall shape.*—Elliptical.

*Quantity.*—About 44.

*Attachment.*—Sessile.

*Average overall length.*—16 cm.

*Average overall width.*—11 to 13 cm.

*Apex.*—Cuspidate.

*Base.*—Acute.

*Margin.*—Strongly undulate.

*Texture.*—Smooth, upper and lower surfaces.

*Appearance.*—Glossy upper surface, matte lower surface.

*Color.*—Color may vary depending on growing conditions. Upper Surface: Glossy Greyed-green, near RHS 189A. Lower Surface: Yellow-Green, near RHS 146B.

*Venation.*—Type: Sunken, below surface of leaf Pattern: Parallel. Color upper side: Yellow-green; closest to RHS 145C. Color under side: Green; closest to RHS 138B.

Inflorescence:

*Shape.*—Pendulous panicles.

*Amount.*—About 7, depending on size of plant.

*Length.*—Average: 25 cm.

*Width.*—Average: 14 cm.

*Color.*—Red-Purple, closest to RHS 64C.

Corolla:

*Number.*—About 50-200 per panicle.

Petals:

*Quantity.*—4-5 per flower.

*Length.*—Average: 13 mm.

*Width.*—Average: 11 mm.

*Overall shape.*—Obovate, asymmetrical.

*Apex.*—Obtuse.

*Color.*—Upper surface: Red-purple closest to RHS 74C. Lower surface: Red-purple closest to RHS 74C.

Sepals:

*Arrangement.*—Growth together, enclosing the ovary.

*Color.*—Near Red-Purple RHS 67A, stippled with White 155D.

Bracts:

*Arrangement.*—Verticillate.

*Quantity.*—4 per crown.

*Length.*—Average 2 to 8 cm.

*Width.*—Average 2 to 3.5 cm. Bracts become smaller closer to the top.

*Shape.*—Elliptical.

*Base shape.*—Clasping.

*Apex shape.*—Acute.

*Color.*—Yellow-white with Red-Purple and Green, near RHS 158D towards the tip with blush of 143A and towards the base 57D.

Bud:

*Length.*—Average: 10 mm.

*Diameter.*—Average: 5 mm.

*Color.*—Red-purple and White, near RHS 57C with 158D at tip.

Peduncles:

*Length.*—Average 18 cm.

*Diameter.*—Average 7 mm.

*Color.*—Green when immature turning Yellow-white when mature with Red-purple anthocyanin, near RHS 144B at base turning 158D towards apex with 57B anthocyanin.

Pedicels:

*Length.*—About 21 mm.

*Diameter.*—Average: 2 mm.

*Color.*—Closest to Red-purple RHS 57D.

REPRODUCTIVE ORGANS

Stamens:

*Number.*—Average 8 per flower.

*Length.*—7 mm.

*Diameter.*—1 mm.

*Color*.—Yellow, with a white base (too small to qualify R.H.S. value).

Anthers:

*Length*.—8 mm.

*Color*.—Violet, closest to RHS 87A.

*Pollen*.—Not visible.

Pistil:

*Number*.—1 per flower.

*Length*.—16 mm.

*Style*.—Length: 12 mm. Color: White, closest to RHS 155D.

*Stigma*.—Shape: Punctiform. Width: <1 mm. Color: White, too small to qualify R.H.S. value.

*Ovary*.—Shape: Obovoid. Position: Inferior. Length: 4 mm. Diameter: 4.5 mm. Color: White; closest to RHS 155D.

OTHER CHARACTERISTICS

Seeds and fruits: No seeds or fruits detected to date.

Disease/pest resistance: Neither resistance nor susceptibility to normal diseases and pests of *Medinilla* observed to date.

Temperature tolerance: Temperatures below 5° C. may damage plants. Upper temperature range unknown, tolerates at least 38° C.

What is claimed is:

1. A new and distinct cultivar of *Medinilla* plant named 'ROYAL TWIST' as herein illustrated and described.

* * * * *